United States Patent
Dreaden et al.

(10) Patent No.: US 12,318,450 B2
(45) Date of Patent: Jun. 3, 2025

(54) PHOTOLYSIS TO UNLOCK CAGED PROTEIN THERAPEUTICS

(71) Applicant: Emory University, Atlanta, GA (US)

(72) Inventors: Erik Dreaden, Atlanta, GA (US); Priscilla Do, Atlanta, GA (US); Lacey Anne Perdue, Atlanta, GA (US)

(73) Assignee: Emory University, Atlanta, GA (US)

( * ) Notice: Subject to any disclaimer, the term of this patent is extended or adjusted under 35 U.S.C. 154(b) by 560 days.

(21) Appl. No.: 17/616,917

(22) PCT Filed: Jun. 4, 2020

(86) PCT No.: PCT/US2020/036077
§ 371 (c)(1),
(2) Date: Dec. 6, 2021

(87) PCT Pub. No.: WO2020/247598
PCT Pub. Date: Dec. 10, 2020

(65) Prior Publication Data
US 2022/0305124 A1  Sep. 29, 2022

Related U.S. Application Data

(60) Provisional application No. 62/968,714, filed on Jan. 31, 2020, provisional application No. 62/857,380, filed on Jun. 5, 2019.

(51) Int. Cl.
*A61K 41/00* (2020.01)
*A61K 38/20* (2006.01)
*A61K 47/60* (2017.01)

(52) U.S. Cl.
CPC ...... *A61K 41/0042* (2013.01); *A61K 38/2013* (2013.01); *A61K 38/2046* (2013.01); *A61K 38/208* (2013.01); *A61K 38/2086* (2013.01); *A61K 47/60* (2017.08)

(58) Field of Classification Search
CPC ............ A61K 38/2013; A61K 38/2046; A61K 38/208; A61K 38/2086; A61K 41/0042; A61K 47/60
See application file for complete search history.

(56) References Cited

U.S. PATENT DOCUMENTS

| | | | |
|---|---|---|---|
| 5,773,308 | A | 6/1998 | Conrad |
| 6,310,083 | B1 | 10/2001 | Kao |
| 2005/0032118 | A1 | 2/2005 | Self |
| 2014/0314709 | A1 | 10/2014 | Loen |
| 2016/0370376 | A1 | 12/2016 | Polukhtin |
| 2017/0340736 | A1 | 11/2017 | Lu |
| 2018/0221503 | A1 | 8/2018 | Kadiyala |
| 2018/0318393 | A1 | 11/2018 | Pierce |
| 2019/0008978 | A1 | 1/2019 | Huang |

FOREIGN PATENT DOCUMENTS

| | | |
|---|---|---|
| WO | 2011107747 | 9/2011 |
| WO | 2012065086 | 5/2012 |
| WO | 2018200462 | 11/2018 |

OTHER PUBLICATIONS

Ankenbruck et al. Optochemical Control of Biological Processes in Cells and Animals, Angew Chem Int Ed Engl. 2018, 57(11):2768-2798.
Backin et al. Copper-free click chemistry for dynamic in vivo imaging, Proc Natl Acad Sci U S A, 2007, 104(43):16793-7.
Buchbinder et al. Therapy with high-dose Interleukin-2 (HD IL-2) in metastatic melanoma and renal cell carcinoma following PD1 or PDL1 inhibition, Journal for ImmunoTherapy of Cancer (2019) 7:49.
Charych et al. NKTR-214, an Engineered Cytokine with Biased IL2 Receptor Binding, Increased Tumor Exposure, and Marked Efficacy in Mouse Tumor Models, Clin Cancer Res, 22(3); 680-90, 2016.
Chauveau et al. Diacylglycerol kinase a establishes T cell polarity by shaping diacylglycerol accumulation at the Immunological synapse, Sci Signal, 2014, 7(340):ra82.
Georgianna et al. Photocleavable Polyethylene Glycol for the Light-Regulation of Protein Function, Bioconjugate Chem, 2010, 21, 1404-1407.
Gorka et al. A Near-IR Uncaging Strategy Based on Cyanine Photochemistry, J. Am. Chem. Soc. 2014, 136, 14153-14159.
Heiskanen et al. Photobiomodulation: Lasers vs Light Emitting Diodes?, Photochem Photobiol Sci, 2018, 17(8):1003-1017.
Jiang et al. Role of IL-2 in cancer immunotherapy, Oncoimmunology, 2016, vol. 5, No. 6, e1163462 (10 pages).
Klatzmann et al. The promise of low-dose interleukin-2 therapy for autoimmune and inflammatory diseases, Nat Rev Immunol, 2015, 15(5):283-94.
Lode et al. Gene therapy with a single chain interleukin 12 fusion protein induces T cell-dependent protective Immunity in a syngeneic model of murine neuroblastoma, Proc. Natl. Acad. Sci. USA vol. 95, pp. 2475-2480, 1998.
Lynn et al. In vivo characterization of the physicochemical properties of TLR agonist delivery that enhance vaccine Immunogenicity, Nat Biotechnol. 2015, 33(11): 1201-1210.
Mancini et al. Controlling the Origins of Inflammation with a Photo-Active Lipopeptide Immunopotentiator, Angew Chem Int Ed Engl. 2015, 54(20): 5962-5965.
Parisi et al. Persistence of adoptively transferred T cells with a kinetically engineered IL-2 receptor agonist, Nature Communications vol. 11, Article No. 660 (2020).
Perdue et al. Optical Control of Cytokine Signaling via Bioinspired, Polymer-Induced Latency, Biomacromolecules. 2020, 21(7):2635-2644.

(Continued)

*Primary Examiner* — Prema M Mertz
(74) *Attorney, Agent, or Firm* — Emory Patent Group

(57) ABSTRACT

This disclosure relates to compositions and uses of caged proteins substituted with a photon decomposing chemical structure wherein the photon decomposing chemical structure is substituted through a linking group to a hydrophilic polymer. In certain embodiments, the caged protein is a proteinaceous agent such as an anticancer agent, cytokine, interleukin, fragment, or fusion thereof.

2 Claims, 7 Drawing Sheets
Specification includes a Sequence Listing.

(56) References Cited

OTHER PUBLICATIONS

PROLEUKIN(R) (aldesleukin) for injection, for intravenous infusion, Prometheus Laboratories Inc., 2012.
Rosenzwajg et al. Immunological and clinical effects of low-dose interleukin-2 across 11 autoimmune diseases in a single, open clinical trial, Ann Rheum Dis 2019, 78:209-217.
Sarode et al., Light Control of Insulin Release and Blood Glucose Using an Injectable Photoactivated Depot, Mol. Pharmaceutics, 2016, 13, 3835-3841.
Tamura et al. Click-crosslinkable and photodegradable gelatin hydrogels for cytocompatible optical cell manipulation in natural environment, Sci Rep, 2015, 5:15060.
Extended European Search Report for EP Patent Application No. 20818017.4, dated Jul. 20, 2023.

fluorescent uncaging reporter design photocage structures 3-(Fmoc-amino)-3-
(2-nitrophenyl)propanoic acid
(NB)

4-{4-[1-(9-Fluorenylmethyloxycarbonylamino)
ethyl]-2-methoxy-5-nitrophenoxy}
butanoic acid
(DMNB)

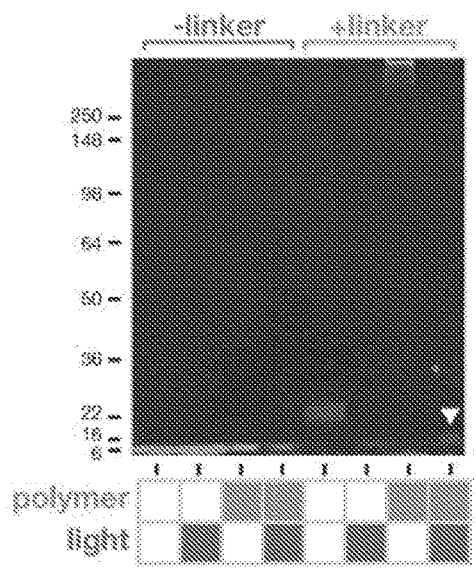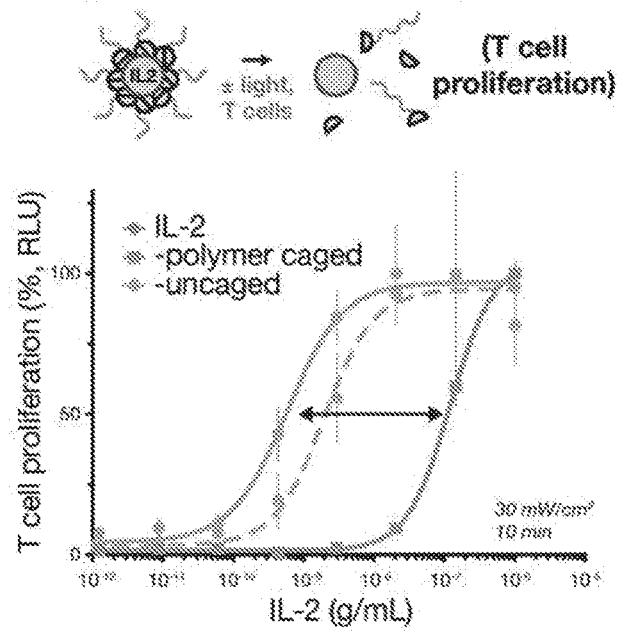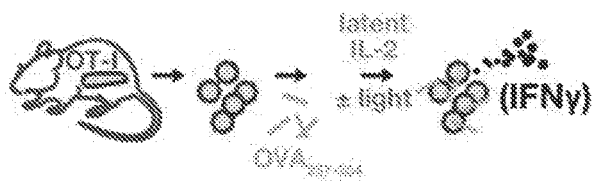
FIG. 3A
FIG. 3B
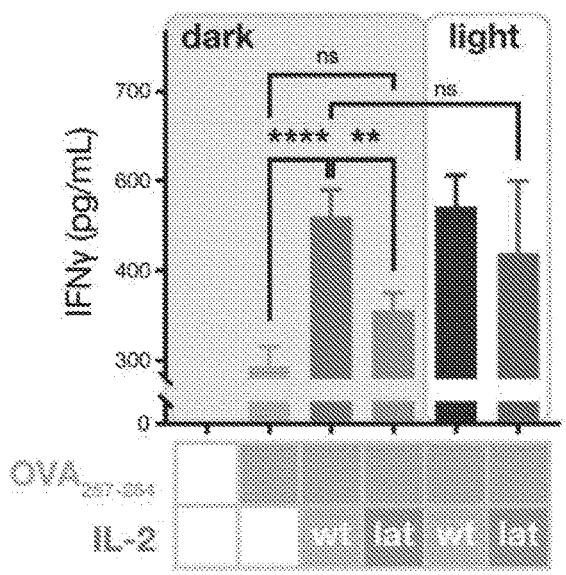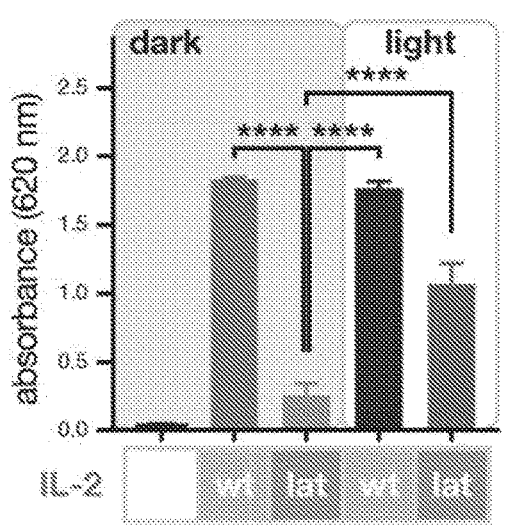
FIG. 3C
FIG. 3D

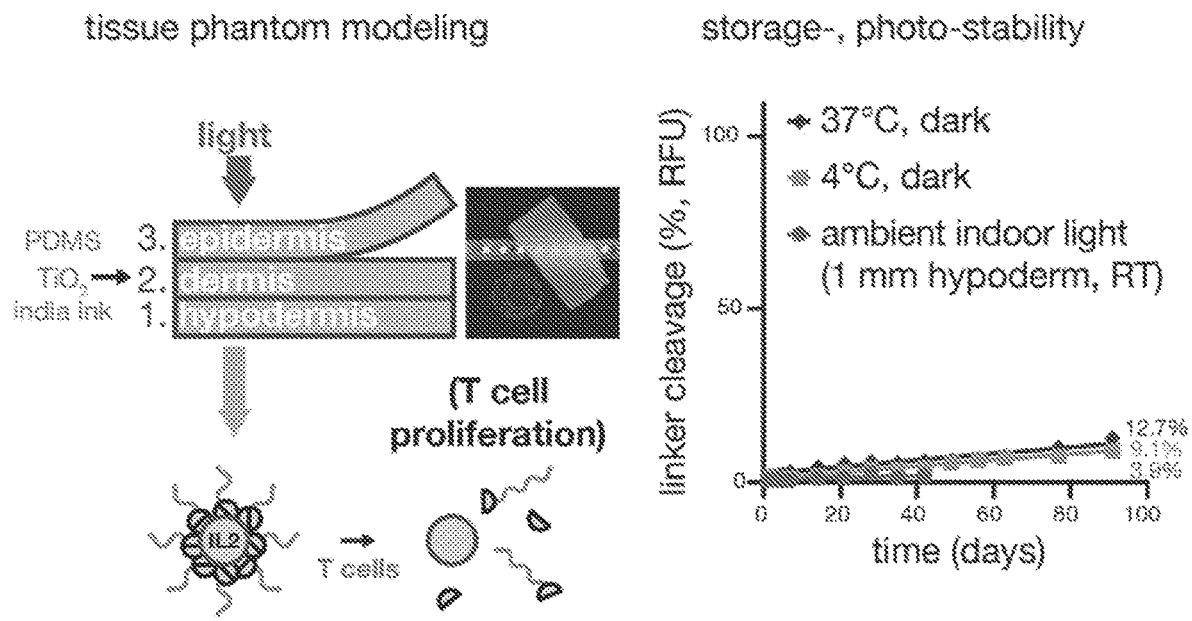
FIG. 5A
FIG. 5B
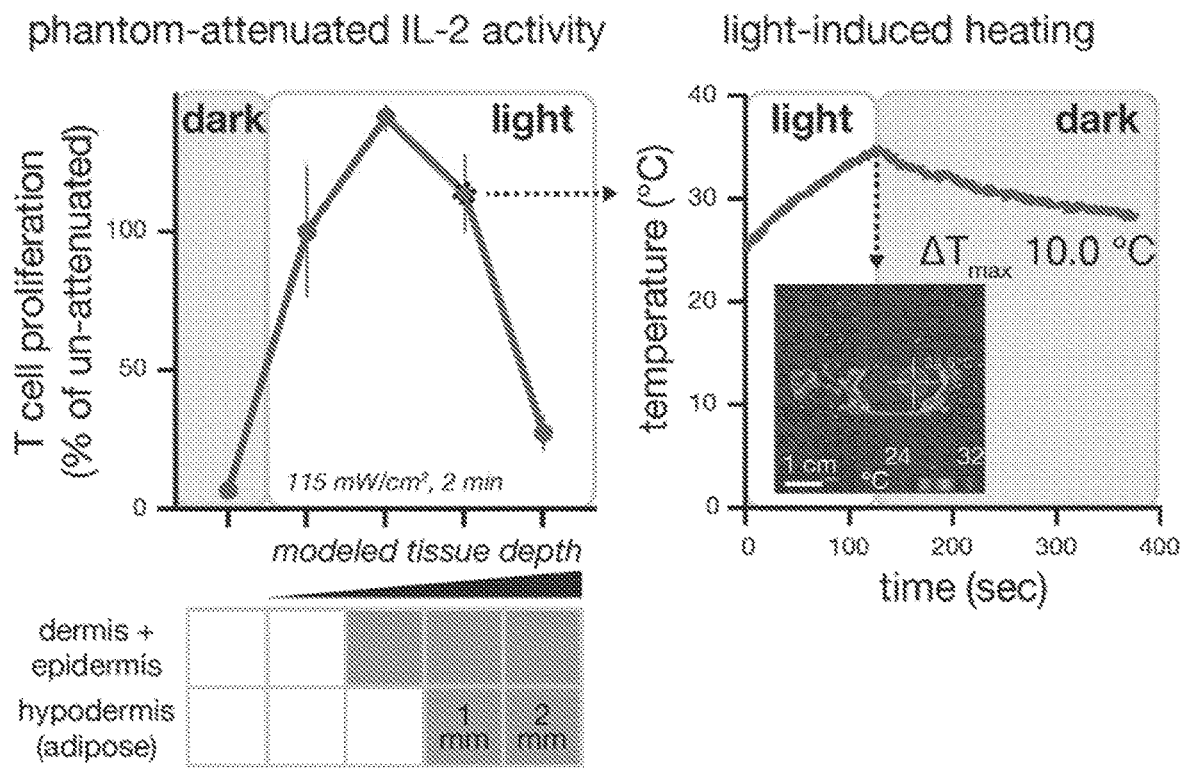
FIG. 5C
FIG. 5D

SEQUENCE LISTING

<160> NUMBER OF SEQ ID NOS: 9

<210> SEQ ID NO 1
<211> LENGTH: 133
<212> TYPE: PRT
<213> ORGANISM: Artificial
<220> FEATURE:
<223> OTHER INFORMATION: Synthetic construct

<400> SEQUENCE: 1

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
                20                  25                  30

Asn Pro Lys Leu Thr Arg Met Leu Thr Phe Lys Phe Tyr Met Pro Lys
            35                  40                  45

Lys Ala Thr Glu Leu Lys His Leu Gln Cys Leu Glu Glu Glu Leu Lys
50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Cys Gln Ser Ile
        115                 120                 125

Ile Ser Thr Leu Thr
        130

<210> SEQ ID NO 2
<211> LENGTH: 197
<212> TYPE: PRT
<213> ORGANISM: Artificial
<220> FEATURE:
<223> OTHER INFORMATION: Synthetic construct

<400> SEQUENCE: 2

Arg Asn Leu Pro Val Ala Thr Pro Asp Pro Gly Met Phe Pro Cys Leu
1               5                   10                  15

His His Ser Gln Asn Leu Leu Arg Ala Val Ser Asn Met Leu Gln Lys
                20                  25                  30

Ala Arg Gln Thr Leu Glu Phe Tyr Pro Cys Thr Ser Glu Glu Ile Asp
            35                  40                  45

His Glu Asp Ile Thr Lys Asp Lys Thr Ser Thr Val Glu Ala Cys Leu
50                  55                  60

Pro Leu Glu Leu Thr Lys Asn Glu Ser Cys Leu Asn Ser Arg Glu Thr
65                  70                  75                  80

Ser Phe Ile Thr Asn Gly Ser Cys Leu Ala Ser Arg Lys Thr Ser Phe
                85                  90                  95

Met Met Ala Leu Cys Leu Ser Ser Ile Tyr Glu Asp Leu Lys Met Tyr
            100                 105                 110

Gln Val Glu Phe Lys Thr Met Asn Ala Lys Leu Leu Met Asp Pro Lys
        115                 120                 125

Arg Gln Ile Phe Leu Asp Gln Asn Met Leu Ala Val Ile Asp Glu Leu
    130                 135                 140

Met Gln Ala Leu Asn Phe Asn Ser Glu Thr Val Pro Gln Lys Ser Ser
145                 150                 155                 160

```
Leu Glu Glu Pro Asp Phe Tyr Lys Thr Lys Ile Lys Leu Cys Ile Leu
            165                 170                 175

Leu His Ala Phe Arg Ile Arg Ala Val Thr Ile Asp Arg Val Met Ser
            180                 185                 190

Tyr Leu Asn Ala Ser
        195

<210> SEQ ID NO 3
<211> LENGTH: 306
<212> TYPE: PRT
<213> ORGANISM: Artificial
<220> FEATURE:
<223> OTHER INFORMATION: Synthetic construct

<400> SEQUENCE: 3

Ile Trp Glu Leu Lys Lys Asp Val Tyr Val Glu Leu Asp Trp Tyr
1               5                   10                  15

Pro Asp Ala Pro Gly Glu Met Val Val Leu Thr Cys Asp Thr Pro Glu
            20                  25                  30

Glu Asp Gly Ile Thr Trp Thr Leu Asp Gln Ser Ser Glu Val Leu Gly
            35                  40                  45

Ser Gly Lys Thr Leu Thr Ile Gln Val Lys Glu Phe Gly Asp Ala Gly
        50                  55                  60

Gln Tyr Thr Cys His Lys Gly Gly Glu Val Leu Ser His Ser Leu Leu
65                  70                  75                  80

Leu Leu His Lys Lys Glu Asp Gly Ile Trp Ser Thr Asp Ile Leu Lys
                85                  90                  95

Asp Gln Lys Glu Pro Lys Asn Lys Thr Phe Leu Arg Cys Glu Ala Lys
            100                 105                 110

Asn Tyr Ser Gly Arg Phe Thr Cys Trp Trp Leu Thr Thr Ile Ser Thr
        115                 120                 125

Asp Leu Thr Phe Ser Val Lys Ser Ser Arg Gly Ser Ser Asp Pro Gln
    130                 135                 140

Gly Val Thr Cys Gly Ala Ala Thr Leu Ser Ala Glu Arg Val Arg Gly
145                 150                 155                 160

Asp Asn Lys Glu Tyr Glu Tyr Ser Val Glu Cys Gln Glu Asp Ser Ala
                165                 170                 175

Cys Pro Ala Ala Glu Glu Ser Leu Pro Ile Glu Val Met Val Asp Ala
            180                 185                 190

Val His Lys Leu Lys Tyr Glu Asn Tyr Thr Ser Ser Phe Phe Ile Arg
        195                 200                 205

Asp Ile Ile Lys Pro Asp Pro Pro Lys Asn Leu Gln Leu Lys Pro Leu
    210                 215                 220

Lys Asn Ser Arg Gln Val Glu Val Ser Trp Glu Tyr Pro Asp Thr Trp
225                 230                 235                 240

Ser Thr Pro His Ser Tyr Phe Ser Leu Thr Phe Cys Val Gln Val Gln
                245                 250                 255

Gly Lys Ser Lys Arg Glu Lys Lys Asp Arg Val Phe Thr Asp Lys Thr
            260                 265                 270

Ser Ala Thr Val Ile Cys Arg Lys Asn Ala Ser Ile Ser Val Arg Ala
        275                 280                 285

Gln Asp Arg Tyr Tyr Ser Ser Ser Trp Ser Glu Trp Ala Ser Val Pro
    290                 295                 300

Cys Ser
305
```

```
<210> SEQ ID NO 4
<211> LENGTH: 115
<212> TYPE: PRT
<213> ORGANISM: Artificial
<220> FEATURE:
<223> OTHER INFORMATION: Synthetic construct

<400> SEQUENCE: 4

Met Asn Trp Val Asn Val Ile Ser Asp Leu Lys Lys Ile Glu Asp Leu
1               5                   10                  15

Ile Gln Ser Met His Ile Asp Ala Thr Leu Tyr Thr Glu Ser Asp Val
            20                  25                  30

His Pro Ser Cys Lys Val Thr Ala Met Lys Cys Phe Leu Leu Glu Leu
        35                  40                  45

Gln Val Ile Ser Leu Glu Ser Gly Asp Ala Ser Ile His Asp Thr Val
    50                  55                  60

Glu Asn Leu Ile Ile Leu Ala Asn Asn Ser Leu Ser Ser Asn Gly Asn
65                  70                  75                  80

Val Thr Glu Ser Gly Cys Lys Glu Cys Glu Glu Leu Glu Glu Lys Asn
                85                  90                  95

Ile Lys Glu Phe Leu Gln Ser Phe Val His Ile Val Gln Met Phe Ile
            100                 105                 110

Asn Thr Ser
        115

<210> SEQ ID NO 5
<211> LENGTH: 6
<212> TYPE: PRT
<213> ORGANISM: Artificial
<220> FEATURE:
<223> OTHER INFORMATION: Synthetic construct

<400> SEQUENCE: 5

Gly Gly Gly Gly Gly Gly
1               5

<210> SEQ ID NO 6
<211> LENGTH: 5
<212> TYPE: PRT
<213> ORGANISM: Artificial
<220> FEATURE:
<223> OTHER INFORMATION: Synthetic construct

<400> SEQUENCE: 6

Gly Gly Gly Gly Thr
1               5

<210> SEQ ID NO 7
<211> LENGTH: 6
<212> TYPE: PRT
<213> ORGANISM: Artificial
<220> FEATURE:
<223> OTHER INFORMATION: Synthetic construct

<400> SEQUENCE: 7

Gly Gly Gly Pro Pro Pro
1               5

<210> SEQ ID NO 8
<211> LENGTH: 7
<212> TYPE: PRT
<213> ORGANISM: Artificial
<220> FEATURE:
```

```
<223> OTHER INFORMATION: Synthetic construct

<400> SEQUENCE: 8

Gly Gly Gly Ala Pro Pro Pro
1               5

<210> SEQ ID NO 9
<211> LENGTH: 8
<212> TYPE: PRT
<213> ORGANISM: Artificial
<220> FEATURE:
<223> OTHER INFORMATION: Synthetic construct

<400> SEQUENCE: 9

Ser Ile Ile Asn Phe Glu Lys Leu
1               5
```

PHOTOLYSIS TO UNLOCK CAGED PROTEIN THERAPEUTICS

CROSS-REFERENCE TO RELATED APPLICATIONS

This application is the National Stage of International Application No. PCT/US2020/036077 filed Jun. 4, 2020, which claims the benefit of U.S. Provisional Application No. 62/968,714 filed Jan. 31, 2020 and U.S. Provisional Application No. 62/857,380 filed Jun. 5, 2019. The entirety of each of these applications is hereby incorporated by reference for all purposes.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy and is hereby incorporated by reference into the specification. The name of the text file containing the Sequence Listing is 19185PCT_ST25.txt. The text file is 8 KB, was created on Jun. 4, 2020, and is being submitted electronically via EFS-Web.

BACKGROUND

Aldesleukin, a human recombinant interleukin-2 (IL-2), is sometimes used in the treatment of metastatic melanoma and renal cell carcinoma. Administration to humans results in multiple effects: lymphocytosis, eosinophilia, thrombocytopenia, and the production of cytokines including tumor necrosis factor, IL-1 and gamma interferon. Treatment with aldesleukin is typically restricted to patients with normal cardiac and pulmonary functions and administered in an intensive care facility where specialists skilled in cardiopulmonary medicine are available. Clinical use is limited due to potential side effects and the complexity of treatment management. Thus, there is a need to identify improvements.

Bossard et al., report conjugates of and IL-2 and a polymer. See WO2012065086.

Ankenbruck et al. report the optochemical control of biological processes in cells and animals. Angew Chemie Int Ed, 2018, 57, 2768-2798.

Sarode et al. report light control of insulin release and blood glucose using an injectable photoactivated depot. Mol Pharm, 2016, 13(11): 3835-3841.

Tamura et al., report click-crosslinkable and photodegradable gelatin hydrogels for cytocompatible optical cell manipulation in natural environment. Sci Rep, 2015, 5:15060.

Georgianna et al. report photocleavable polyethylene glycol for the light-regulation of protein function. Bioconjugate Chem, 2010, 21, 8, 1404-1407.

References cited herein are not an admission of prior art.

SUMMARY

This disclosure relates to compositions and uses of caged proteins substituted with a photon decomposing chemical structure wherein the photon decomposing chemical structure is substituted through a linking group to a hydrophilic polymer. In certain embodiments, the caged protein is a proteinaceous agent such as an anticancer agent, cytokine, interleukin, fragment, or fusion thereof.

In certain embodiments, this disclosure relates to compositions comprising a caged cytokine, such as an interferon, interleukin, growth factor, fragment, or fusion thereof, wherein a nitrogen of an N-terminal amine, an amino acid lysine, histidine, arginine, a hydroxyl group of serine, threonine, and tyrosine, or the sulfur of cysteine, or combinations thereof of the caged cytokine are substituted with a photon decomposing chemical structure wherein the photon decomposing chemical structure is substituted through a linking group to a hydrophilic polymer. In certain embodiments, the cytokine is interleukin-2, interleukin-7, interleukin-12, interleukin-15, fragment, or fusion thereof. In certain embodiments, the hydrophilic polymer is polyethylene glycol. In certain embodiments, the photon decomposing chemical structure has a 2-nitrobenzyl group.

In certain embodiments, this disclosure relates to methods of treating a cytokine related disease or condition such as cancer or a tumor, type 1 or type 2 diabetes, rheumatoid arthritis, ankylosing spondylitis, systemic lupus erythematosus, vasculitis, or atherosclerosis comprising: administering an effective amount of a caged protein to a subject diagnosed with a cytokine related disease or condition, wherein the caged protein is substituted with a photon decomposing chemical structure wherein the photon decomposing chemical structure is substituted through a linking group to a hydrophilic polymer; and directing a photon to an area of the body of the subject containing diseased cells or tissue such as cancerous cells or a tumor decomposing the photon decomposing chemical structure providing a sufficient amount of a proteinaceous anticancer agent in area of the cancer or tumor.

In certain embodiments, this disclosure relates to methods of treating cancer or a tumor comprising: administering an effective amount of a caged protein to a subject diagnosed with cancer or a tumor, wherein a nitrogen of an N-terminal amine, an amino acid lysine, histidine, arginine, or the sulfur of cysteine, or combinations thereof of the caged protein is substituted with a photon decomposing chemical structure wherein the photon decomposing chemical structure is substituted through a linking group to a hydrophilic polymer; and directing a photon to an area of the body of the subject containing cancerous cells or a tumor decomposing the photon decomposing chemical structure providing a sufficient amount of a proteinaceous anticancer agent in area of the cancer or tumor.

In certain embodiments, this disclosure relates to methods of treating cancer or a tumor comprising: administering an effective amount of a caged cytokine to a subject diagnosed with cancer or a tumor, wherein the caged cytokine is substituted with a photon decomposing chemical structure wherein the photon decomposing chemical structure is substituted through a linking group to a hydrophilic polymer, and directing a photon to an area of the body of the subject containing cancerous cells or a tumor decomposing the photon decomposing chemical structure providing a sufficient amount of a cytokine in area of the cancer or tumor. In certain embodiments, the cytokine is interleukin-2, interleukin-7, interleukin-12, or interleukin-15. In certain embodiments, the cancer is melanoma, and the cytokine is interleukin-2. In certain embodiments, the subject is diagnosed with metastatic melanoma. In certain embodiments, the cancer is renal cell carcinoma, and the cytokine is interleukin-2. In certain embodiments, the subject is diagnosed with metastatic renal cell carcinoma. In certain embodiments, the cancer is neuroblastoma, and the cytokine is interleukin-12.

In certain embodiments, the caged protein or caged cytokine is administered in combination with another anticancer agent or cell or T cell to be used in non-cell based or cell based cancer therapies such as adoptive T cell therapy. In certain embodiments, combine administration with T cells include T cells transfected with a vector encoding a chimeric antigen receptor and the T cells are expressing the chimeric antigen receptor. In certain embodiments, the caged cytokine is administered in combination with an immune checkpoint inhibitor. In certain embodiments, the checkpoint inhibitor is an anti-CTLA-4 antibody, anti-PD-1 antibody, anti-PD-L1 antibody, or combinations thereof. In certain embodiments, the checkpoint inhibitor is ipilimumab, nivolumab, pembrolizumab, cemiplimab, atezolizumab, durvalumab, avelumab, or combinations thereof.

In certain embodiments, this disclosure relates to in vitro methods: providing a cell and a caged protein, wherein the caged protein is substituted with a photon decomposing chemical structure wherein the photon decomposing chemical structure is substituted through a linking group to a hydrophilic polymer; and directing a photon to an area in the cell or around the cell decomposing the photon decomposing chemical structure providing a sufficient amount of a protein in the cell or around the area of the cell.

In certain embodiments, this disclosure relates to in vitro methods comprising: providing a cell or tissue and a caged cytokine, wherein the caged cytokine is substituted with a photon decomposing chemical structure wherein the photon decomposing chemical structure is substituted through a linking group to a hydrophilic polymer; and directing a photon to an area in the cell or tissue around the cell decomposing the photon decomposing chemical structure providing a sufficient amount of a cytokine in the cell or around the area of the cell.

In certain embodiments, this disclosure relates to pharmaceutical compositions comprising a pharmaceutically acceptable excipient and a caged cytokine substituted with a photon decomposing chemical structure wherein the photon decomposing chemical structure is substituted through a linking group to a hydrophilic polymer.

BRIEF DESCRIPTION OF THE SEVERAL VIEWS OF THE DRAWINGS

FIG. 3A shows electrophoretic mobility shift demonstrating linker- and polymer-dependent modification of IL-2, as well as light-dependent restoration (arrowhead) of wild-type protein mobility as measured by polyacrylamide gel electrophoresis.

FIG. 3B shows data on polymer-dependent repression and light-induced restoration of IL-2 activity as measured by CTLL-2 T cell proliferation (24 h).

FIG. 3C shows data on the effect of latent IL-2 and uncaged IL-2 (1000 IU/mL molar equivalents) on $OVA_{257-264}$ antigen-specific T cell activation as measured ex vivo by ELISA of OT-I splenocyte-secreted interferon gamma (IFNγ).

FIG. 3D shows data indicating latent IL-2 induced near baseline levels of STAT5 transcriptional activity, while that from the light-uncaged protein was comparable to that from wild type IL-2.

FIG. 5A is an illustration of multilayered tissue phantom construction.

FIG. 5B shows data on the stability of 5 kDa poly(ethylene glycol) polymer photocages under prolonged, aqueous storage and under conditions simulating ambient, indoor light exposure of superficial veins (1 mm depth) as measured by cleavage-induced fluorescence dequenching.

FIG. 5C shows the effect of tissue phantom light attention on latent IL-2 activity as measured by CTLL-2 T cell proliferation (24 h).

FIG. 5D shows data on superficial heating of multilayered tissue phantoms of the indicated thickness as measured by forward-looking infrared imaging.

DETAILED DISCUSSION

Figure 1A:
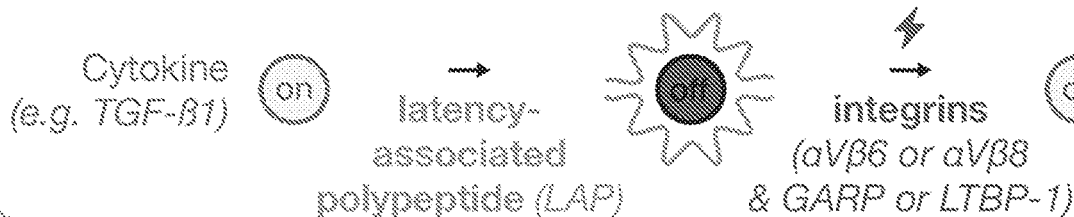
FIG. 1A illustrates transforming growth factor-β1 (TGF-β1) transmitting tissue- and cell-specific cytokine signals via association of with latency associated peptide (LAP) which sterically shields and later disassociates from TGF-β1 in response to traction forces caused by the binding of αVβ6 or αVβ8 integrins with either cell membrane-bound GARP or extracellular matrix-bound LTBP-1.
Figure 1B:
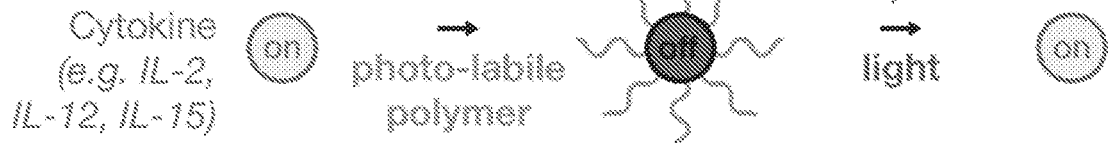
FIG. 1B illustrates a strategy for the induction of reversible latency in cytokines with pleiotropic effects via modification with end-modified, photo-labile polymers.
Figure 1C:
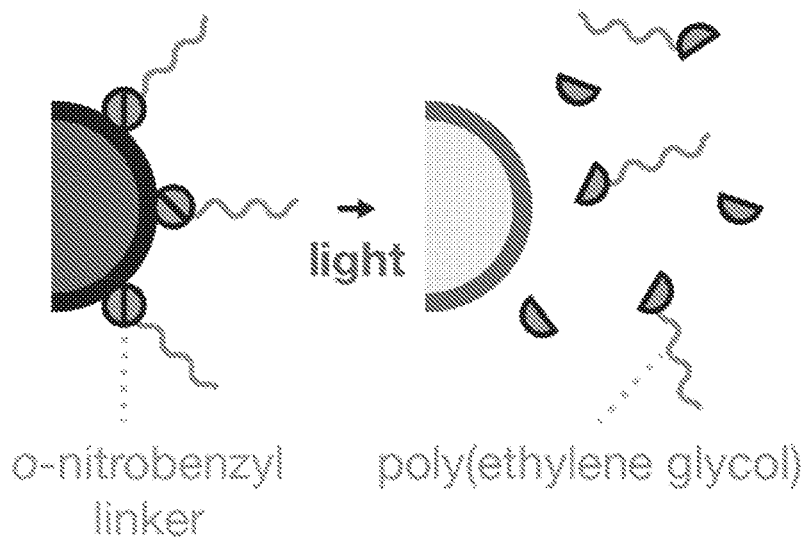
FIG. 1C illustration of the traceless modification strategy used here whereby 20 kDa poly(ethylene glycol) polymer chains are appended to cytokine lysine residues via o-nitrobenzyl groups
Figure 1D:
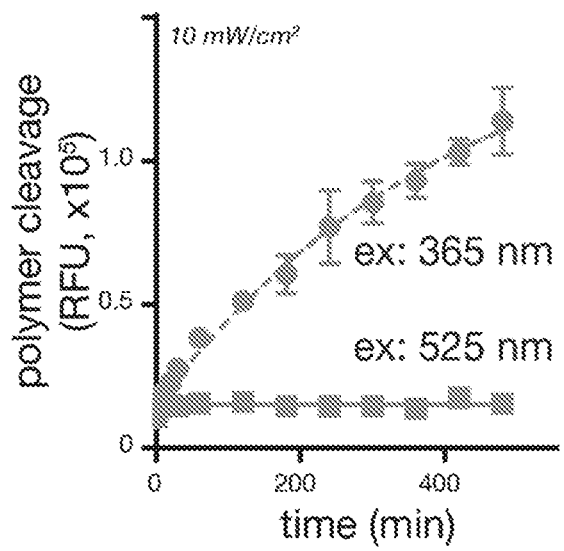
FIG. 1D shows data indicating the caging polymer is rapidly degraded by blue, but not green, LED light as measured by cleavage-induced fluorescence de-quenching.
Figure 1E:
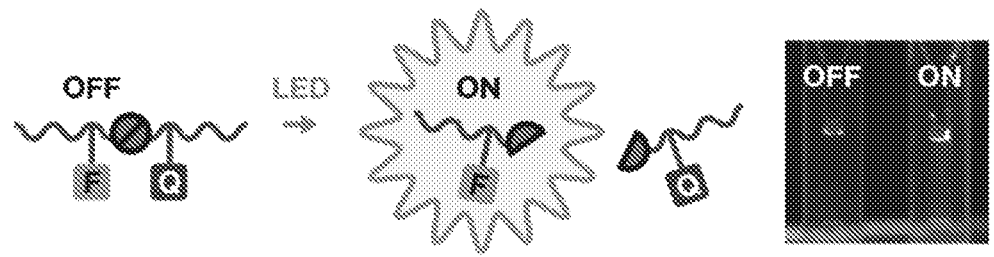
FIG. 1E illustrates light-induced cleavage of two o-nitrobenzyl-linked poly(ethylene glycol) polymers and cleavage-induced fluorescence de-quenching reporters. Optical images of irradiated and non-irradiated samples are shown. Chemical structures of (left) NB and (right) DMNB photocages.
Figure 1E:
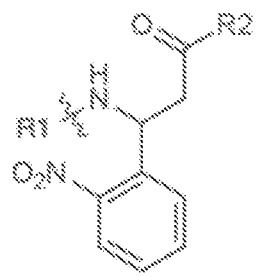
Figure 1E:
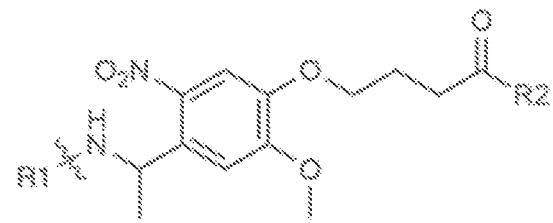
Figure 1F:
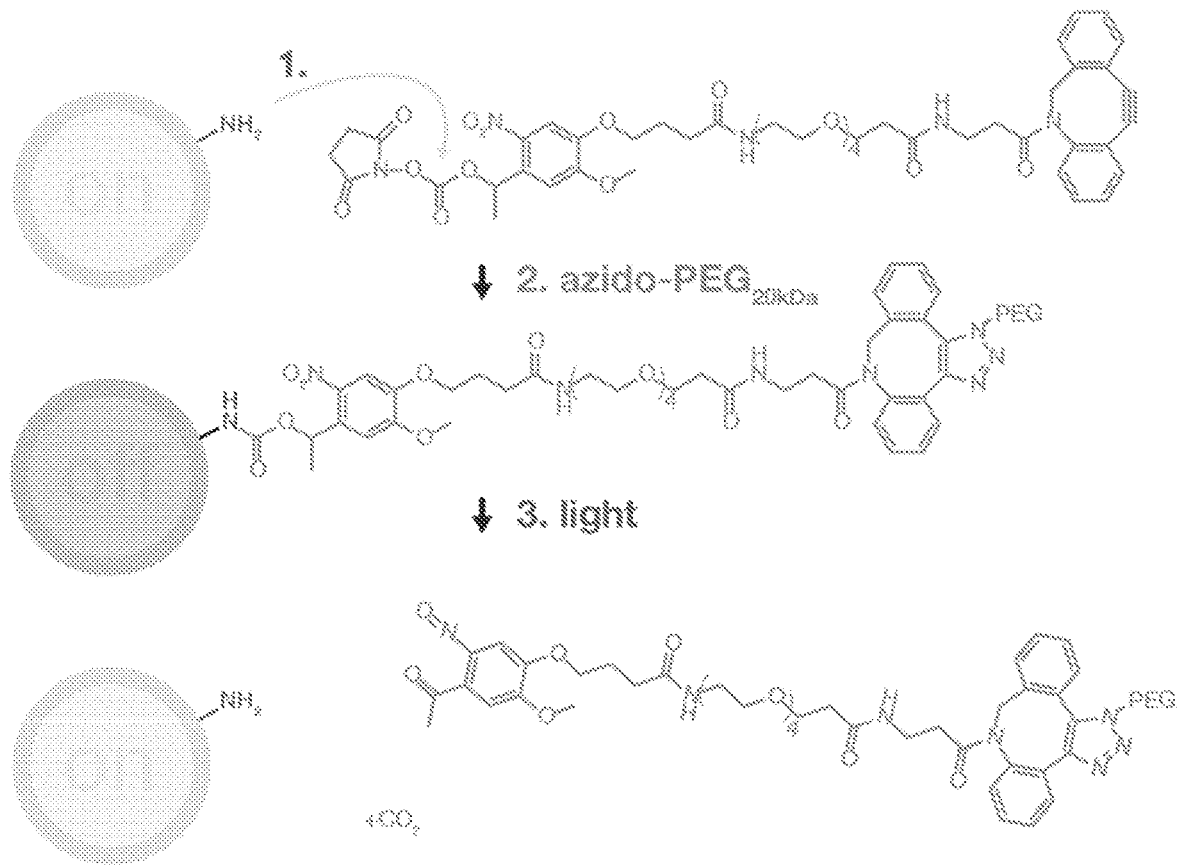
FIG. 1F illustrates photo-labile polymer modification of cytokines. Traceless modification strategy whereby cytokine lysine residues are modified with NHS-nitrobenzyl-DBCO groups via carbodiimide coupling, followed by conjugation with mPEG-$N_3$ (20 kDa) via copper free click chemistry.
Figure 2A:
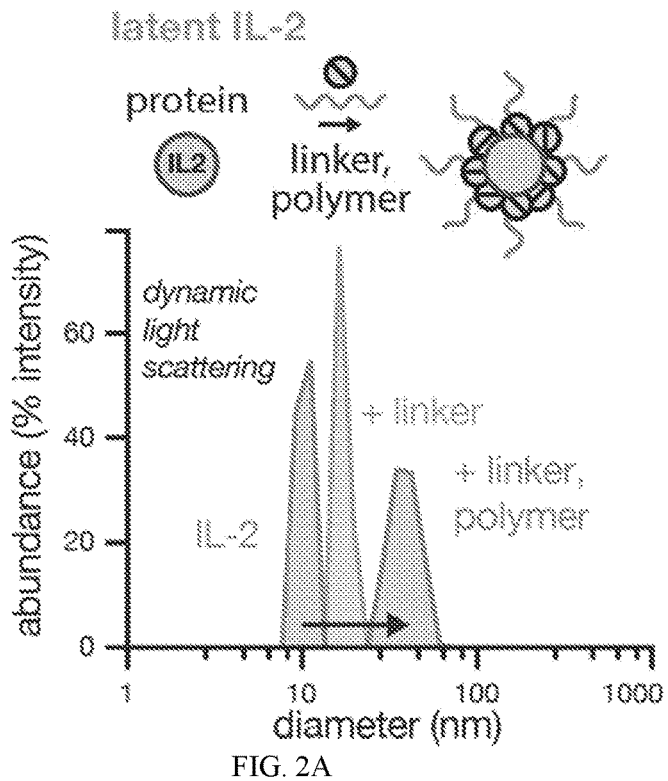
FIG. 2A shows data indicating polymer-induced latency augments cytokine size. Stepwise increase in IL-2 hydrodynamic size upon linker and polymer conjugation as measured by dynamic light scattering.
Figure 2B:
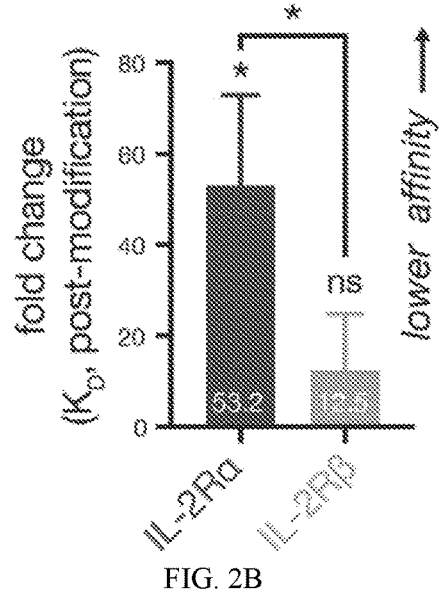
FIG. 2B shows sensorgrams depicting binding kinetics for IL-2 or latent IL-2 association/dissociation with IL-2Rα (CD25) or IL-2Rβ (CD122) as fold-change in post-modification binding affinity.
Figure 2C:
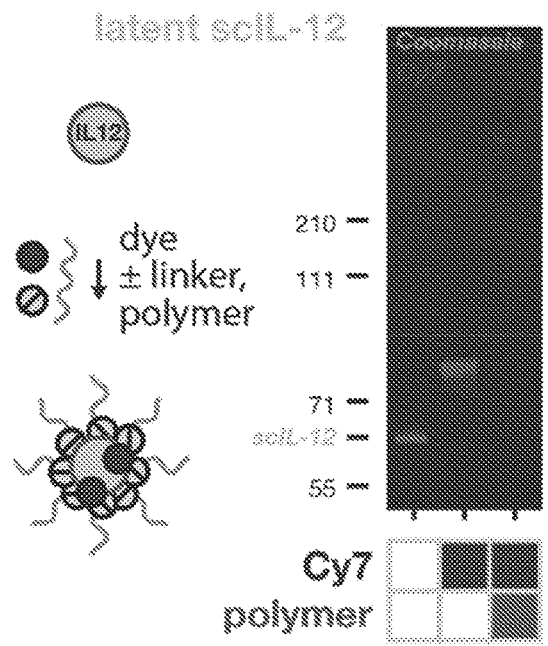
FIG. 2C shows electrophoretic mobility shift demonstrating Cy7 dye- and polymer-dependent modification of scIL-12 as measured by polyacrylamide gel electrophoresis.
Figure 2D:
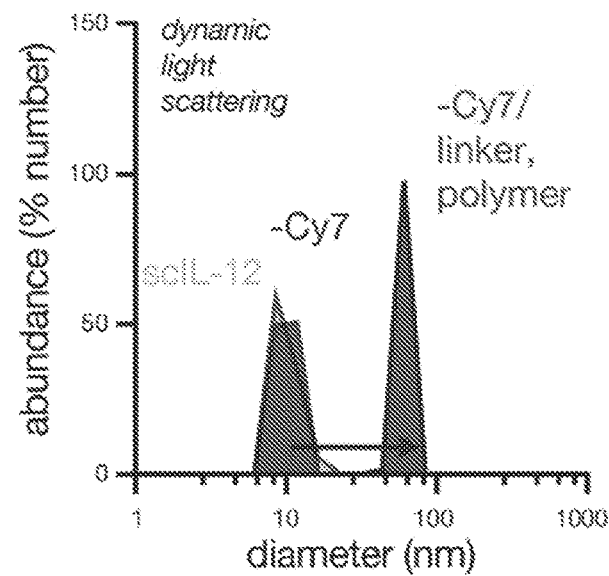
FIG. 2D shows increase in scIL-12 hydrodynamic size following Cy7 conjugation with or without linker/polymer modification as measured by dynamic light scattering.
Figure 2E:
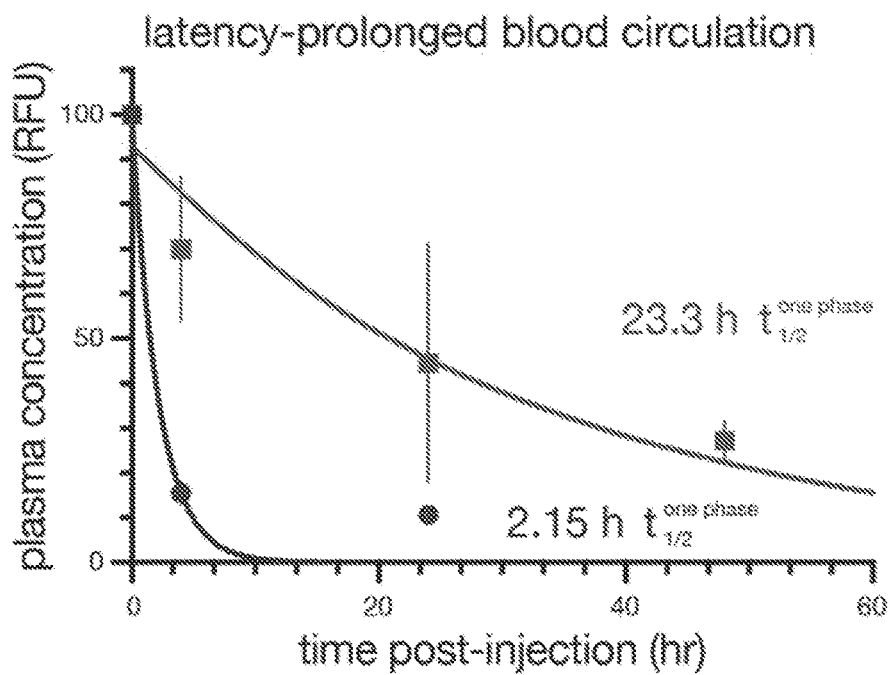
FIG. 2E shows data on plasma pharmacokinetics of Cy7-labeled scIL-12 modified with or without linker/polymer following intravenous injection into (C57BL/6 mice) illustrating prolonged circulation following photolabile polymer modification.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. In this specification and in the claims that follow, reference will be made to a number of terms that shall be defined to have the following meanings unless a contrary intention is apparent.

"Subject" refers to any animal, preferably a human patient, livestock, rodent, monkey or domestic pet.

"Cancer" refers any of various cellular diseases with malignant neoplasms characterized by the proliferation of cells. Cancer may or may not be present as a tumor mass with a defined boundary. It is not intended that the diseased cells must actually invade surrounding tissue and metastasize to new body sites. Cancer can involve any tissue of the body and have many different forms in each body area. Within the context of certain embodiments, whether "cancer is reduced" may be identified by a variety of diagnostic manners known to one skill in the art including, but not limited to, observation the reduction in size or number of tumor masses or if an increase of apoptosis of cancer cells observed, e.g., if more than a 5% increase in apoptosis of cancer cells is observed for a sample compound compared to a control without the compound. It may also be identified by a change in relevant biomarker or gene expression profile, such as PSA for prostate cancer, HER2 for breast cancer, or others.

As used herein, the terms "treat" and "treating" are not limited to the case where the subject (e.g., patient) is cured and the disease is eradicated. Rather, embodiments, of the present disclosure also contemplate treatment that merely reduces symptoms, and/or delays disease progression.

As used herein, the term "combination with" when used to describe administration with an additional treatment means that the agent may be administered prior to, together with, or after the additional treatment, or a combination thereof.

The term "effective amount" refers to that amount of a compound or pharmaceutical composition described herein that is sufficient to affect the intended application including, but not limited to, disease treatment, as illustrated below. In relation to a combination therapy, an "effective amount" indicates the combination of agent results in synergistic or additive effect when compared to the agents individually. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The specific dose will vary depending on, for example, the particular compounds chosen, the dosing regimen to be followed, whether it is administered in combination with other agents, timing of administration, the tissue to which it is administered, and the physical delivery system in which it is carried.

A "chemotherapy agent," "chemotherapeutic," "anti-cancer agent," or the like, refer to molecules that are recognized to aid in the treatment of a cancer. Contemplated examples include the following molecules or derivatives such as abemaciclib, abiraterone acetate, methotrexate, paclitaxel, adriamycin, acalabrutinib, brentuximab vedotin, ado-trastuzumab emtansine, aflibercept, afatinib, netupitant, palonosetron, imiquimod, aldesleukin, alectinib, alemtuzumab, pemetrexed disodium, copanlisib, melphalan, brigatinib, chlorambucil, amifostine, aminolevulinic acid, anastrozole, apalutamide, aprepitant, pamidronate disodium, exemestane, nelarabine, arsenic trioxide, ofatumumab, atezolizumab, bevacizumab, avelumab, axicabtagene ciloleucel, axitinib, azacitidine, carmustine, belinostat, bendamustine, inotuzumab ozogamicin, bevacizumab, bexarotene, bicalutamide, bleomycin, blinatumomab, bortezomib, bosutinib, brentuximab vedotin, brigatinib, busulfan, irinotecan, capecitabine, fluorouracil, carboplatin, carfilzomib, ceritinib, daunorubicin, cetuximab, cisplatin, cladribine, cyclophosphamide, clofarabine, cobimetinib, cabozantinib-S-malate, dactinomycin, crizotinib, ifosfamide, ramucirumab, cytarabine, dabrafenib, dacarbazine, decitabine, daratumumab, dasatinib, defibrotide, degarelix, denileukin diftitox, denosumab, dexamethasone, dexrazoxane, dinutuximab, docetaxel, doxorubicin, durvalumab, rasburicase, epirubicin, elotuzumab, oxaliplatin, eltrombopag olamine, enasidenib, enzalutamide, eribulin, vismodegib, erlotinib, etoposide, everolimus, raloxifene, toremifene, panobinostat, fulvestrant, letrozole, filgrastim, fludarabine, flutamide, pralatrexate, obinutuzumab, gefitinib, gemcitabine, gemtuzumab ozogamicin, glucarpidase, goserelin, propranolol, trastuzumab, topotecan, palbociclib, ibritumomab tiuxetan, ibrutinib, ponatinib, idarubicin, idelalisib, imatinib, talimogene laherparepvec, ipilimumab, romidepsin, ixabepilone, ixazomib, ruxolitinib, cabazitaxel, palifermin, pembrolizumab, ribociclib, tisagenlecleucel, lanreotide, lapatinib, olaratumab, lenalidomide, lenvatinib, leucovorin, leuprolide, lomustine, trifluridine, olaparib, vincristine, procarbazine, mechlorethamine, megestrol, trametinib, temozolomide, methylnaltrexone bromide, midostaurin, mitomycin C, mitoxantrone, plerixafor, vinorelbine, necitumumab, neratinib, sorafenib, nilutamide, nilotinib, niraparib, nivolumab, tamoxifen, romiplostim, sonidegib, omacetaxine, pegaspargase, ondansetron, osimertinib, panitumumab, pazopanib, interferon alfa-2b, pertuzumab, pomalidomide, mercaptopurine, regorafenib, rituximab, rolapitant, rucaparib, siltuximab, sunitinib, thioguanine, temsirolimus, thalidomide, thiotepa, trabectedin, valrubicin, vandetanib, vinblastine, vemurafenib, vorinostat, zoledronic acid, or combinations thereof such as cyclophosphamide, methotrexate, 5-fluorouracil (CMF); doxorubicin, cyclophosphamide (AC); mustine, vincristine, procarbazine, prednisolone (MOPP); sdriamycin, bleomycin, vinblastine, dacarbazine (ABVD); cyclophosphamide, doxorubicin, vincristine, prednisolone (CHOP); bleomycin, etoposide, cisplatin (BEP); epirubicin, cisplatin, 5-fluorouracil (ECF); epirubicin, cisplatin, capecitabine (ECX); methotrexate, vincristine, doxorubicin, cisplatin (MVAC).

The terms, "interleukin-2" and "IL-2" refers to a cytokine (about 15-kDa) predominantly secreted by activated T cells and that is involved in the cell-mediated immune responses. Interleukin-2 precursor [*Homo sapiens*] has NCBI Reference Sequence: NP_000577.2 where amino acids 1-20 are a secretory signal peptide (SP). Other variants of IL-2 include F42K, R38A, V69A, Q74P, Q74R, Q74H, Q74N, Q74S, L80I, L80F, L80V, R81I, R81T, R81D, N88D, L85V, I86V, I89V, I92F, V93I V91K, I24V, P65H, C125V, C125A, and C125S with amino acid positions as provided for in SEQ ID NO: 1 which does not contain the SP.

APTSSSTKKTQLQLEHLLLDLQMILNGIN-NYKNPKLTRMLTFKFYMPKKATELK HLQCLEEELKPLEEVLNLAQSKNFHLRPRDLISNIN-VIVLELKGSETTFMCEYADETATIV EFLNRWITFCQSI-ISTLT (SEQ ID NO: 1). Aldesleukin is a human recombinant interleukin-2 product of approximately 15,300 daltons. The chemical name is des-alanyl-1, serine-125 human interleukin-2. This recombinant form differs from native interleukin-2 in the following ways: a) not glycosylated because it is derived from *E. coli*; b) has no N-terminal alanine; the codon for this amino acid was deleted during the genetic engineering procedure; c) the molecule has serine substituted for cysteine at amino acid position 125. In certain embodiments, IL-2 includes variants of SEQ ID NO: 1 which have greater than 80, 85, 90, 95, 96, 97, 98, 99 or greater sequence identity or similarity. In certain embodiments, IL-2 is complexed with, conjugated to, or fused to IL-2R alpha protein.

A single chain IL-12 fusion protein is the recombinant protein of p35 and p40 subunits fused with a flexible an amino acid linker [e.g., (glycine$_4$ serine)$_3$ having 15 amino acids]. See e.g., Lode et al., Gene therapy with a single chain interleukin 12 fusion protein induces T cell-dependent protective immunity in a syngeneic model of murine neuroblastoma Proc. Natl. Acad. Sci. USA, 1998, Vol. 95, pp. 2475-2480. The p35 subunit has the amino acid sequence (SEQ ID NO: 2):

RNLPVATPDPGMFPCLHHSQNLLRAVSNMLQKAR-QTLEFYPCTSEEIDHEDITKD KTSTVEACLPLELTK-NESCLNSRETSFITNGSCLASRKTSFMMALCLSSI-YEDLKMYQVE FKTMNAKLLMDPKRQIFLDQNMLAVIDELMQAL-NFNSETVPQKSSLEEPDFYKTKIKLC ILLHAFRI-RAVTIDRVMSYLNAS; and the p40 subunit has the amino acid sequence (SEQ ID NO: 3) IWELKKDVYVVELDWYPDAPGEMVVLTCDTPEED-GITWTLDQSSEVLGSGKTLTIQVK EFGDAGQYTCHKGGEVLSHSLLLLHKKEDGIW-STDILKDQKEPKNKTFLRCEAKNYSGR FTCWWLT-TISTDLTFSVKSSRGSSDPQGVTCGAATL-SAERVRGDNKEYEYSECQEDSA CPAAEESLPIEVMVDAVHKLKYENYTSSFFIR-DIIKPDPPKNLQLKPLKNSRQVEVSWEY PDTW-STPHSYFSLTFCVQVQGKSKREKKDRVFTDKTSATVI-CRKNASISVRAQDRYYSS SWSEWASVPCS. In certain embodiments, IL-12 includes p35 variants of SEQ ID NO: 2 which have greater than 80, 85, 90, 95, 96, 97, 98, 99 or greater sequence identity or similarity and/or p40 variants of SEQ ID NO: 3 which have greater than 80, 85, 90, 95, 96, 97, 98, 99 or greater sequence identity or similarity.

IL-15 is an immunomodulating cytokine that stimulates the proliferation of T lymphocytes and shares some biological properties with IL-2, e.g., IL-15 exerts its biological activities on T cells. Human recombinant IL-15 is available commercially as a protein with an amino acid sequence (SEQ ID NO: 4)

MNWVNVISDLKKIEDLIQSMHIDATLYTESDVHP-SCKVTAMKCFLLELQVISLES GDASIHDTVEN-LIILANNSLSSNGNVTESGCKECEELEEKNIKE-FLQSFVHIVQMFINTS. In certain embodiments, IL-15 includes variants of SEQ ID NO: 1 which have greater than 80, 85, 90, 95, 96, 97, 98, 99 or greater sequence identity or similarity. In certain embodiments, IL-15 is complexed with, conjugated to, or fused to IL-15R alpha protein.

Variants may include 1 or 2 amino acid substitutions or conserved substitutions. Variants may include 3 or 4 amino acid substitutions or conserved substitutions. Variants may include 5 or 6 or more amino acid substitutions or conserved substitutions. Variant include those with not more than 1% or 2% of the amino acids are substituted. Variant include those with not more than 3% or 4% of the amino acids are substituted. Variants include proteins with greater than 80%, 89%, 90%, 95%, 98%, or 99% identity or similarity.

Variants can be tested by mutating a vector to produce appropriate codon alternatives for polypeptide translation. Active variants and fragments can be identified with a high probability using computer modeling. Shihab et al. report an online genome tolerance browser. BMC Bioinformatics. 2017, 18(1):20. Ng et al. report methods of predicting the effects of amino acid substitutions on protein function. Annu Rev Genomics Hum Genet. 2006, 7:61-80. Teng et al. Approaches and resources for prediction of the effects of non-synonymous single nucleotide polymorphism on protein function and interactions. Curr Pharm Biotechnol. 2008, 9(2):123-33.

Guidance in determining which and how many amino acid residues may be substituted, inserted or deleted without abolishing biological activity may be found using computer programs well known in the art, for example, RaptorX, ESyPred3D, HHpred, Homology Modeling Professional for HyperChem, DNAStar, SPARKS-X, EVfold, Phyre, and Phyre2 software. See also Saldano et al. Evolutionary Conserved Positions Define Protein Conformational Diversity, PLoS Comput Biol. 2016, 12(3):e1004775; Marks et al. Protein structure from sequence variation, Nat Biotechnol. 2012, 30(11):1072-80; Mackenzie et al. Curr Opin Struct Biol. 2017, 44:161-167 Mackenzie et al. Proc Natl Acad Sci USA. 113(47):E7438-E7447 (2016); Joseph et al. J R Soc Interface. 2014, 11(95):20131147, Wei et al. Int. J. Mol. Sci. 2016, 17(12), 2118. Variants can be tested in functional assays. Certain variants have less than 10%, and preferably less than 5%, and still more preferably less than 2% changes (whether substitutions, deletions, and so on).

In certain embodiments, term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number of positions in the window of comparison (i.e., the window size), and multiplying the result by 100 to yield the percentage of sequence identity. In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG (SEQ ID NO: 5) and GGGGT (SEQ ID NO: 6) have a sequence identity of 4 out of 5 or 80%. For example, the polypeptides GGGPPP (SEQ ID NO: 7) and GGGAPPP (SEQ ID NO: 8) have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q. The amino acid groups are also considered conserved substitutions.

Proteins and cytokines disclosed herein, e.g., IL-2, IL-12, and IL-15, can be derived from non-recombinant methods and from recombinant methods and the invention is not limited in this regard. In addition, the moiety can be derived from human sources, animal sources, and plant sources. Proteins and cytokines can be derived non-recombinantly. For example, it is possible to isolate IL-2 from biological systems and otherwise obtain IL-2 from cultured media. See, for example, the procedures described in U.S. Pat. No. 4,401,756 and in Pauly et al. (1984) J. Immunol Methods 75(1):73-84. The IL-2 moiety can be derived from recombinant methods. See, for example, U.S. Pat. No. 5,614,185, the disclosure and the Experimental provided herein.

Proteins and cytokines can be expressed in bacterial, mammalian, yeast, and plant expression systems. The expression can occur via exogenous expression (when the host cell naturally contains the desired genetic coding) or via endogenous expression. Although recombinant-based methods for preparing proteins can differ, recombinant methods typically involve constructing the nucleic acid encoding the desired polypeptide or fragment, cloning the nucleic acid into an expression vector, transforming a host cell (e.g., plant, bacteria, yeast, transgenic animal cell, or mammalian cell such as Chinese hamster ovary cell or baby hamster kidney cell), and expressing the nucleic acid to produce the desired polypeptide or fragment. Methods for producing and expressing recombinant polypeptides in vitro and in pro-karyotic and eukaryotic host cells are known to those of ordinary skill in the art.

To facilitate identification and purification of the recombinant polypeptide, nucleic acid sequences that encode for an epitope tag or other affinity binding sequence can be inserted or added in-frame with the coding sequence, thereby producing a fusion protein comprised of the desired polypeptide and a polypeptide suited for binding. Fusion proteins can be identified and purified by first running a mixture containing the fusion protein through an affinity column bearing binding moieties (e.g., antibodies) directed against the epitope tag or other binding sequence in the fusion proteins, thereby binding the fusion protein within the column. Thereafter, the fusion protein can be recovered by washing the column with the appropriate solution (e.g., acid) to release the bound fusion protein. The recombinant polypeptide can also be purified by lysing the host cells, separating the polypeptide, e.g., by ion-exchange chromatography, affinity binding approaches, hydrophobic interaction approaches, and thereafter identify by MALDI or western blot, and collecting the polypeptide. These and other methods for identifying and purifying recombinant polypeptides are known to those of ordinary skill in the art.

Depending on the system used to express proteins can be unglycosylated or glycosylated and either may be used. Proteins and cytokines can advantageously be modified to include and/or substitute one or more amino acid residues such as, for example, lysine, cysteine and/or arginine, in order to provide facile attachment of the polymer to an atom within the side chain of the amino acid. In addition, proteins and cytokines can be modified to include a non-naturally occurring amino acid residue. Techniques for adding amino acid residues and non-naturally occurring amino acid residues are well known to those of ordinary skill in the art.

Hydrophilic polymers contain polar or charged functional groups, rendering them soluble in water. Examples include polyethylene glycol, polylactides, polyglycolide, poly(ε-caprolactone), poly(2-methoxyethyl acrylate), poly(tetrahydrofurfuryl acrylate), poly(2-methacryloyloxyethyl phosphorylcholine), poly(p-dioxanone), poly(serine methacrylate), poly[oligo(ethylene glycol) vinyl ether], poly{[2-(methacryloyloxy)ethyl], copolymers of ethylene glycol and propylene glycol, poly(oxyethylated polyol), poly (olefmic alcohol), poly(vinylpyrrolidone), poly(hydroxyalkylmethacrylamide), poly(hydroxyalkylmethacrylate), poly (saccharides), poly(alpha-hydroxy acid), and poly(vinyl alcohol).

"PEG," "polyethylene glycol" and "poly(ethylene glycol)" as used herein, are interchangeable and encompass any nonpeptidic water-soluble poly(ethylene oxide). Typically, PEGs for use in accordance with the invention comprise the following structure "—(OCH$_2$CH$_2$)$_n$—" where (n) is 2 to 4000. As used herein, PEG also includes "—CH$_2$CH$_2$—O (CH$_2$CH$_2$O)$_n$—CH$_2$CH$_2$—" and "—(OCH$_2$CH$_2$)$_n$O—," depending upon whether or not the terminal oxygens have been displaced, e.g., during a synthetic transformation. Throughout the specification and claims, it should be remembered that the term "PEG" includes structures having various terminal or "end capping" groups and so forth. The term "PEG" also means a polymer that contains a majority, that is to say, greater than 50%, of —OCH$_2$CH$_2$— repeating subunits. With respect to specific forms, the PEG can take any number of a variety of molecular weights, as well as structures or geometries such as "branched," "linear," "forked," "multifunctional," and the like, to be described in greater detail below.

Typically, the weight-average molecular weight of the water-soluble polymer is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000

Daltons. For any given water-soluble polymer, PEGs having a molecular weight in one or more of these ranges are preferred.

The terms "end-capped" and "terminally capped" are interchangeably used herein to refer to a terminal or end-point of a polymer having an end-capping moiety. Examples of end-capping moieties include alkoxy (e.g., methoxy, ethoxy and benzyloxy), as well as aryl, heteroaryl, and the like. It must be remembered that the end-capping moiety may include one or more atoms of the terminal monomer in the polymer [e.g., the end-capping moiety "methoxy" in $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescent dyes, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleoylphosphatidylcholine, dipalmitoylphosphatidylcholine, distearoylphosphatidylcholine, behenoylphosphatidylcholine, arachidoylphosphatidylcholine, and lecithin.

Photon Decomposing Chemical Structure

Photolysis is a chemical reaction wherein covalent bonds are broken down by an interaction of photons with target molecules. Photons capable of inducing photolysis reactions include visible light, near-infrared light, ultraviolet light, X-rays, and gamma rays. In certain embodiments, this disclosure relates to a photon decomposing chemical structure wherein the photon decomposing chemical structure is substituted through a linking group to a hydrophilic polymer.

In certain embodiments, the photon decomposing chemical structure has a 2-nitrobenzyl group. In certain embodiments, the photon decomposing chemical structure has 1-(4-hydroxy-5-methoxy-2-nitrophenyl)ethoxy)carbonyl, wherein the 4-hydroxy is substituted through a linking group to a hydrophilic polymer.

In certain embodiments, the photon decomposing chemical structure has formula I or formula II,

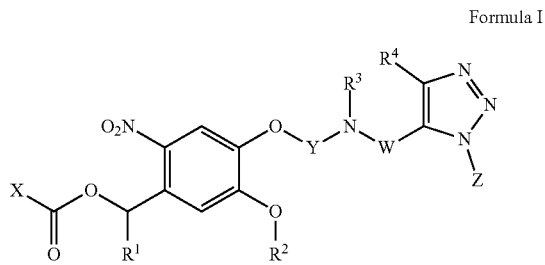

Formula I

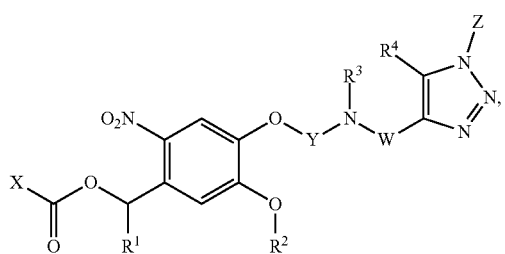

Formula II wherein
X is a nitrogen from a protein;
Y is a linking group;
Z is the hydrophilic polymer or a linking group linked to the hydrophilic polymer;
W is a linking group;
$R^1$ is hydrogen or alkyl;
$R^2$ is alkyl or aryl optionally substituted; and
$R^3$ is hydrogen, alkyl; or
$R^3$ and $R^4$ come together with the attached atoms to form a heterocyclyl.

A "linking group" refers to any variety of molecular arrangements that can be used to bridge to molecular moieties together. An example formula may be —$R_n$— wherein R is selected individually and independently at each occurrence as: —$CR_nR_n$—, —$CHR_n$—, —CH—, —C—, —$CH_2$—, —$C(OH)R_n$, —C(OH)(OH)—, —C(OH)H, —$C(Hal)R_n$—, —C(Hal)(Hal)-, —C(Hal)H—, —$C(N_3)R_n$—, —$C(CN)R_n$—, —C(CN)(CN)—, —C(CN)H—, —$C(N_3)(N_3)$—, —$C(N_3)$H—, —O—, —S—, —N—, —NH—, —$NR_n$—, —(C=O)—, —(C=NH)—, —(C=S)—, —(C=$CH_2$)—, which may contain single, double, or triple bonds individually and independently between the R groups. If an R is branched with an $R_n$ it may be terminated with a group such as —$CH_3$, —H, —CH=$CH_2$, —CCH, —OH, —SH, —$NH_2$, —$N_3$, —CN, or -Hal, or two branched Rs may form an aromatic or non-aromatic cyclic structure. It is contemplated that in certain instances, the total Rs or "n" may be less than 100 or 50 or 25 or 10. Examples of linking groups include bridging alkyl groups and alkoxyalkyl groups.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like.

In certain embodiments, the photon decomposing chemical structure has formula III or formula IV,

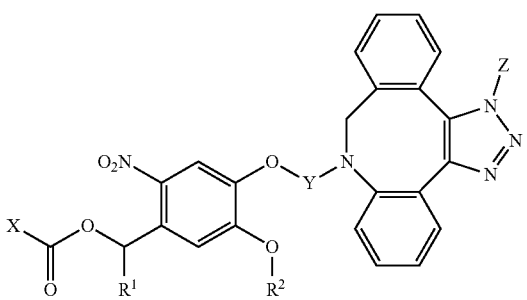

Formula III

-continued

Formula IV

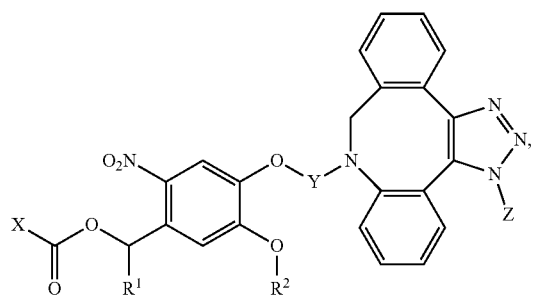

wherein
X is a nitrogen or sulfur from the protein;
Y is a linking group;
Z is a hydrophilic polymer or a linking group linked to the hydrophilic polymer;
$R^1$ is alkyl; and
$R^2$ is alkyl.

In certain embodiments, the photon decomposing chemical structure has formula V, Formula V

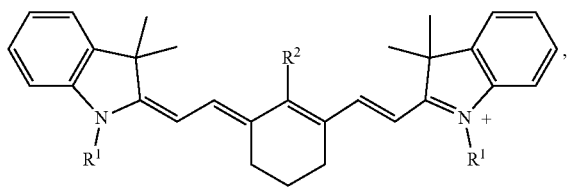

wherein
$R^1$ is, individually and independently at each occurrence, alkyl, sulfonylalkyl, hydrophilic polymer, linking group to a hydrophilic polymer, or —Y—X; and
$R^2$ is halogen, amine, alkyl, hydrophilic polymer, linking group to a hydrophilic polymer, or —Y—X;
X is a nitrogen or sulfur from the protein; and
Y is a linking group.

"Sulfonylalkyl" refers to a sulfonyl attached through an alkyl bridge (i.e., -alkylSO₃H) or salt thereof such as —(CH₂)₄SO₃⁻.

In certain embodiments, any of the above chemical structures may be optionally substituted with one or more, the same or different, substituents.

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NR$_a$R$_b$, —NR$_a$C(=O)R$_b$, —NR$_a$C(=O)NR$_a$NR$_b$, —NR$_a$C(=O)OR$_b$, —NR$_a$SO₂R$_b$, —C(=O)R$_a$, —C(=O)OR$_a$, —C(=O)NR$_a$R$_b$, —OC(=O)NR$_a$R$_b$, —OR$_a$, —SR$_a$, —SO$_{Ra}$, —S(=O)₂R$_a$, —OS(=O)₂R$_a$ and —S(=O)₂OR$_a$ or salt thereof.

R$_a$ and R$_b$ in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

Light-Responsive Caged Proteins as Prodrug Therapeutics

A prodrug-based approach was developed to cage immune signal effector proteins with light-responsive polymers that de-shield in response to specific colors of focused LED or laser light. This can be used to spatially and temporally constrain the activation of cytokines in the body and in cell culture. The synthetic biomolecules can be used as immunotherapies that can drug patient tumors in a more tissue-exclusive and patient personalized fashion.

In certain embodiments, this disclosure relates to immune modulatory proteins to which a chemical linker is appended that allows for further attachment of a polymer, both or one of which alter or block normal protein activity and extend the duration of blood circulation. In response to exposure with light of the appropriate wavelength, the linker and/or polymer fragment, altering or recovering the activity of the pro-drug (or caged) protein. The caging of recombinant IL-2, IL-12, and IL-15 protein are exemplified. One may use of photocleavable groups based on nitrobenzyl or cyanine (substituted 2-((E)-2-((E)-3-(2-((E)-3,3-dimethylindolin-2-ylidene)ethylidene)cyclohex-1-en-1-yl)vinyl)-3,3-dimethyl-3H-indol-1-ium by near-infrared light, e.g., 650 and 900 nm). Shielding (or caging) polymers include poly(ethylene glycol) ranging in size from 5 kDa to 30 kDa. Photo-exposure methods include LED (365 nm) and pulsed laser (740-770 nm) excitation.

Caged IL-2 protein has an approximately 20-fold increase in size following pro-drug modification, measuring 40 nm in hydrodynamic diameter and 162 kDa in size via DLS and PAGE, respectively. Prolonged circulation and improved tumor accumulation compared with the native protein (15.5 kDa) are hoped to result in less frequent dosing and less prevalent or severe toxic side effects. IL-2 in vitro activity on T cells was blunted approximately 1,000-fold following polymer conjugation and was near fully recovered following light-induced uncaging (10 min, 30 mW/cm², 365 nm). Photopatterning experiments demonstrate that light-induced protein uncaging can be performed with micrometer-scale resolution and that light-induced T cell activation can be spatially constrained within cell culture.

Polymer-induced latency blunts corresponding JAK/STAT pathway signaling and CD8+ or regulatory T cell activation ex vivo. Brief LED light exposure can be used to de-repress these effects. High spatial and temporal control of cytokine signaling can be used modulate T cell priming/expansion directly at sites of disease or at associated secondary lymphoid organs. Such strategies may also extend to chemokines which can serve to further orchestrate effective adaptive immune responses against pathogens or tumors. A minimum spatial resolution of photoactivation approaching that of a single immune cell was achieved without the use of focusing optics. Although light scattering and diffusion would limit such dimensions in vivo, strong feasibility to constrain cytokine activation to mm-scale diseased tissues and lymph nodes is anticipated. This is supported by tissue phantom studies performed here, showing efficient light-induced de-repression at modeled subdermal depths of as high as 1 mm, sufficient in many instances for activation within human superficial veins as well as within transcutaneous or some transepithelial disease sites.

Serendipitously, it was found that polymer-induced latency, alone, biased the affinity of latent IL-2 towards IL-2Rβ (CD122) and away from IL-2Rα (CD25). As CD8+ T cells express IL-2Rβγ and immunosuppressive Tregs constitutively express IL-2Rαβγ, these findings suggest that the latent cytokine may improve CD8+/Treg ratios which are prognostically favorable in many cancers and correlate with clinical responses to immune checkpoint blockade therapy in patients. It is believed that atypically high density of solvent-accessible lysine resides at the IL-2/IL-2Rα interface preferentially induce steric hindrance with the receptor subunit via appended polymer chains.

In addition to demonstrating rapid and efficient cytokine photo-activation, polymer-photocages used here were highly stable under conditions simulating both aqueous storage and venous ambient light exposure. Compared with other more rapidly hydrolyzable PEG/IL-2 conjugates (e.g. NKTR-214), these findings are encouraging and lead to integration with wearable or implanted light-delivery devices which modulate drug activation. Bioinspired, polymer-induced latency was able to prolong scIL-12 plasma circulation approximately 11-fold, potentially precluding the need for frequent, high dosing and improving tissue drug exposure in treatment settings.

A strategy for polymer-induced cytokine latency and photo-induced reactivation is described. Cytokine activity can be precisely regulated using light, which may be further adapted by conjugating additional photo-labile linkers which absorb light at wavelengths with higher tissue penetrance. In certain embodiments the cytokines may further to contain photo-labile linkers derived from other fluorescent dyes.

Described herein is a generalizable strategy for light-induced cytokine de-repression that can be used to spatially and temporally control the activity of otherwise pleiotropic immune signaling molecules. As research tools, the technologies described here hold great potential to improve our ability to understand and manipulate basic immune biology, and to optically reprogram immune responses ex vivo and in vitro. As therapies, they serve as long-acting pro-drugs or tissue-selective immune modulators, both alone or in combination with other immunotherapies.

Optical Control of Cytokine Signaling Via Polymer-Induced Latency

Reported herein is a strategy whereby cytokines are chemically modified with photo-labile polymers that mimic the induction of protein latency while attached, then de-shield to recover protein activity in response to monochromatic light exposure. This approach enables both the magnitude and the duration of cytokine signals to be tuned on-demand, with high spatial resolution, and can be rapidly adapted to a range of additional cytokine or chemokine proteins.

To assess the feasibility of polymer-induced cytokine latency and subsequent light-induced activation (FIG. 1A-1C, 1E), the cleavage efficiency of two distinct polyethylene glycol (PEG) polymers modified to exhibit fluorescence dequenching following the cleavage of o-nitrobenzyl linker derivatives when exposed with blue LED light. In phosphate buffer, these polymer cages exhibited fast cleavage kinetics (k'~0.028-0.12 $min^{-1}$) that was both power-dependent and highly wavelength-discriminant (FIG. 1D). Based on these results, a traceless chemical modification strategy was devised which appended high molecular weight PEG (20 kDa) to cytokine lysine residues by way of a dialkoxy-substituted 2-nitrobenzyl linker (FIG. 1F), selected due to its red-shifted absorption and enhanced water solubility compared with other o-nitrobenzyl cages.

To demonstrate polymer-induced cytokine latency, recombinant human IL-2 was selected as a candidate for photo-labile polymer modification due to its lack of a known latency binding partner and its pleiotropic effects in vivo, for example its simultaneous immunostimulatory effects exerted via cytotoxic T cells and immunosuppressive effects exerted through regulatory T cells. IL-2 has demonstrated clinical benefit in patients with melanoma, renal cell cancer, and neuroblastoma. These benefits are greatly limited by rapid excretion of IL-2 which necessitates continuous or frequent high-dosing and thus toxicity and complex treatment management. Polymer-induced IL-2 latency could be used to both control IL-2 signaling ex vivo, as well as improve the safety or therapeutic potential of this and related cytokines via prolonged circulation.

Following modification of IL-2, a stepwise increase in size upon both linker and polymer conjugation was observed as measured by both polyacrylamide gel electrophoresis and dynamic light scattering (FIG. 2A). Latent IL-2 was approximately three-fold larger than the wild type protein in overall diameter, thus well above the lower size limit for renal clearance in humans. the binding affinity of latent IL-2 with two of its cognate receptor subunits, IL-2Rα (CD25) and IL-2Rβ (CD122) were evaluated via biolayer interferometry (FIG. 2B). Strikingly, binding affinity of IL-2 towards IL-2Rα was decreased approximately 53-fold following latency-induction, whereas that towards IL-2Rβ was not significantly altered. This serendipitous result suggests that, relative to wild type IL-2, latent IL-2 maintains biased activity towards CD8+ T cells that express IL-2Rβγ and dampened activity towards immunosuppressive $T_{regs}$ that constitutively express IL-2Rαβγ.

Having demonstrated that polymer-induced latency can modulate cognate receptor binding affinity, the effect of polymer-induced latency was characterized on in vivo cytokine circulation using IL-12, another recombinant cytokine under clinical investigation which similarly suffers from rapid clearance and systemic, off-target toxic effects. To monitor cytokine circulation in vivo, a single-chain variant of the cytokine, scIL-12, was dye-labeled both with and without photo-labile polymer modification (20 kDa PEG, FIG. 2C). Cy7-labeling only nominally increased scIL-12 size as measured by polyacrylamide gel electrophoresis and dynamic light scattering, whereas combined dye and photo-labile polymer modification increased hydrodynamic size to 44 nm (FIG. 2D), well above the renal clearance size threshold in humans and rodents. The circulation of latent scIL-12 was monitored following tail vein injection in C57BL/6 mice, finding that the latent cytokine experienced 16-fold increase in circulation half-life following polymer-modification (FIG. 2E). These results suggest that the prolonged circulation of scIL-12 may (i) obviate the need for frequent, high dosing and (ii) improve tissue accumulation of the drug in therapeutic settings.

Photo-Activation of Latent Cytokines

After characterizing the effects of polymer-induced cytokine latency, the recovery of functional protein activity was examined using CTLL-2 T cells that depend on both IL-2 and IL-2Rα for growth. Following latency-induction, an approximate $10^3$-fold drop in rhIL-2 activity was observed as measured by CTLL-2 T cell proliferation (24 h); however, subsequent LED irradiation to uncage IL-2 near fully restored both native molecular weight and capacity for induced T cell proliferation (FIG. 3A, 3B). In vivo, as little as a 10-fold change in rhIL-2 activity is necessary in order to functionally modulate fate decisions in T cells that lead to either memory or effector fate; thus, the near three logs of dynamic range observed here in vitro suggest that latent cytokines may be used to control T cell biology ex vivo or modulate therapeutic activity of the recombinant protein. To further demonstrate the feasibility of this approach, latency-induction was examined with rhIL-15, finding that small molecule linker addition, alone, was sufficient to achieve 5- to 20-fold modulation of CTLL-2 T cell dose-dependent proliferation (24 h).

To further explore the therapeutic potential of latent IL-2, experiments were performed to determine its ability to promote antigen-specific immunity using OT-I T cell receptor transgenic mice which generate clonal CD8+ T cells specific to SIINFEKL ($OVA_{257-264}$) (SEQ ID NO: 9), an octameric peptide from ovalbumin. OT-I splenocytes were pulsed with OVA257-264 and treated with either wild type or latent IL-2, with or without LED irradiation, and IFNγ was measured as an indication of the extent of T cell activation. While latent IL-2 had no significant effect on antigen-specific T cell activation, that from the light-uncaged protein was comparable and statistically indistinguishable from wild type IL-2 (FIG. 3C).

To ascertain whether the activity of latent IL-2 on OT-I T cells was like the wild type protein, JAK/STAT pathway-dependent, its effect was examined on HEK293 cells engineered to express all three subunits of human IL-2R as well as JAK3 and STAT5. In response to STAT5 activation, these cells secrete alkaline phosphatase which can be spectrophotometrically detected using a chromogenic substrate. The trends in reporter cell response observed in these studies closely match those observed in activated OT-I T cells. Latent IL-2 induced near baseline levels of STAT5 transcriptional activity, while that from the light-uncaged protein was comparable to that from wild type IL-2 (FIG. 3D). Together, these data support that LED irradiation can de-repress IL-2 latency, promote antigen-specific immunity, and re-activate JAK/STAT pathway signaling.

Feasibility of In Situ Cytokine De-Repression

Figure 4A:
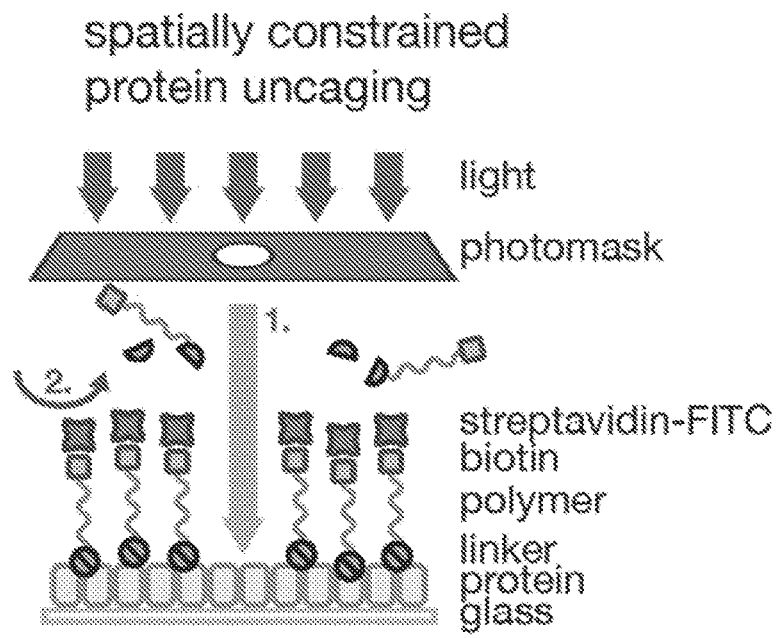
FIG. 4A shows an illustration of experiments to visualize protein latency and photo-induced de-repression.
Figure 4B:
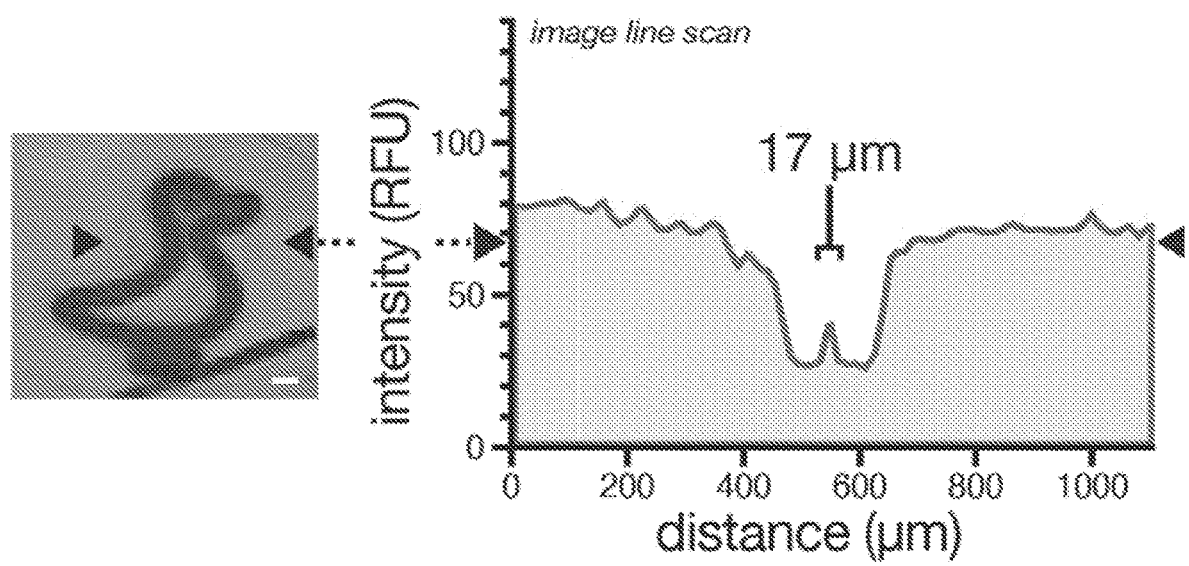
FIG. 4B shows a fluorescence micrograph and a corresponding image line scan image indicating regions of latent and uncaged protein as measured by epifluorescence microscopy. This indicates light-induced uncaging enables precise, local control of protein activity.

Having shown that cytokine latency can be used to temporally control immune cell signaling, experiments were performed to determine whether the spatial resolution with which cytokine activity could be constrained. A latent analog of IL-2 was prepared using bovine serum albumin modified with a photo-labile PEG containing a biotin tag at its distal end (FIG. 4A). Following immobilization onto glass slides, irradiation through a custom photolithographic mask, and streptavidin-FITC staining, spatially constrained protein uncaging was observed with resolution at or below the typical dimensions of single human immune cells (<17 μm, FIG. 4B). These results suggest that cytokine activity can be de-repressed with high spatial and temporal control using this synthetic modification approach.

To explore the effects of tissue light attenuation on latent IL-2 activation, a series of silicone-based phantoms were fabricated that mimic light transmission through human dermis, epidermis, and hypodermis at wavelengths specific to the polymer photocages described here (FIG. 5A). Using these models, the stability of 5 kDa PEG photocages were examined under prolonged, aqueous storage conditions and under conditions simulating ambient indoor light exposure of superficial veins (1 mm hypodermis depth). High stability of aqueous solutions in cold storage were observed with <10% total uncaging of polymer linkages after 90 days (FIG. 5B). Given that many clinical products have post-reconstitution shelf-lives of just hours to days, the storage durations observed here appear sufficient for large-scale in vivo testing. Comparably low levels of polymer cleavage were observed under conditions mimicking non-deliberate light exposure of superficial veins over 6 weeks (<4%). These latter data suggest that polymer-induced latency may be maintained in vivo over time scales necessary for light-constrained cytokine de-repression.

To model the feasibility of light-induced cytokine uncaging in vivo, the activity of latent IL-2 was examined following photo-exposure through tissue phantoms modeling human skin and subcutaneous tissue. Near full recovery of IL-2 activity was observed at depths corresponding to 1 mm beneath the dermis as measured by CTLL-2 T cell proliferation (FIG. 5C). These findings are significant as such depths, in many cases, correspond to the minimal light attenuation experienced at human superficial veins as well as within transcutaneous or some transepithelial tumors. Moreover, as the light irradiance required for activation through tissue phantoms induced only a small temperature increase (Tmax 10.0 C, FIG. 5D).

Polymer-Induced Latency

Recombinant cytokines were sequentially modified with photo-labile linkers and polymers via carbodiimide coupling and Cu-free click chemistry. Cytokines were reacted with a 2-nitrobenzyl linker displaying both N-hydroxysuccinimidyl (NHS) ester and dibenzocyclooctyne (DBCO) substituents followed by addition of poly(ethylene glycol) methyl ether azide. Reaction conditions are described as molar equivalents relative to total lysine residues or total DBCO groups.

Recombinant IL-2 was modified via dilution in 150 mM sodium phosphate buffer (pH 8.5) containing 0.5 mM SDS and addition of 3 eq. of photo-labile linker to a maximum DMSO concentration of 5% v/v. 10 eq. of poly(ethylene glycol) methyl ether azide (20 kDa) dissolved in PBS (pH 7.4) was then added and allowed to react. All cytokine modification steps were allowed to proceed overnight at 4° C. with rotary agitation (800 rpm). In some experiments, excess PEG was removed via DBCO-agarose beads.

Recombinant scIL-12 was modified via dilution in 150 mM sodium phosphate buffer (pH 8.5) containing 0.5 mM SDS and addition of (i) 1 eq. of NHS-sulfoCy7 to 5% v/v DMSO or (ii) addition of 1 eq. of NHS-sulfoCy7 and 5 eq. of photo-labile linker to 5% v/v DMSO. 5 eq. of poly (ethylene glycol) methyl ether azide (20 kDa) dissolved in PBS (pH 7.4) was then added and allowed to react. Excess dye was removed via desalting column (7 k MWCO, Pierce).

Recombinant IL-15 was modified via dilution in buffer containing 10 mM $NaH_2PO_4$/150 mM NaCl and addition of 20 eq. of photo-labile linker to 5% v/v DMSO.

Photo-Induced Polymer Cleavage

Detailed characterization of light-induced polymer cleavage was monitored via fluorescence de-quenching of 5FAM- and CPQ2-modified polyethylene glycol (5 kDa). Polymers containing the photo-labile linkers were obtained using linker reagents. Modified polymers (azido-G-K(CPQ2)-NB/DMNB-PEO4-G-K(5FAM)-G-C-PEG5k) were >96% pure as measured by RP-HPLC. Samples were dissolved to 500 nM in ultrapure water and irradiated within quartz cuvettes using collimated, light-emitting diodes. Fluorescence de-quenching was measured on a plate reader. Cleavage kinetics were fit to a one-phase decay using software. Storage and stability measurements were similarly obtained from solution aliquots maintained in on a laboratory benchtop, incubator, or laboratory refrigerator. Samples were covered with aluminum plate film or tissue phantoms and exposed to fluorescent overhead office lights as indicated.

The invention claimed is:

1. A composition comprising a caged cytokine wherein the caged cytokine is conjugated to a photon decomposing chemical structure, wherein the photon decomposing chemical structure is conjugated through a linking group to a hydrophilic polymer, wherein the cytokine is interleukin-2, interleukin-7, interleukin-12, or interleukin-15, and wherein the photon decomposing chemical structure has a 2-nitrobenzyl group.

2. The composition of claim 1, wherein the hydrophilic polymer is polyethylene glycol.

* * * * *